United States Patent [19]
Ravichandran et al.

[11] Patent Number: 4,808,645
[45] Date of Patent: Feb. 28, 1989

[54] 6-(1-HYDRO-2,2,6,6-TETRAALKYL-PIPERI-DINE-4-OXY)DIBENZODIOXAPHOSPHE-PIN AND DIOXAPHOSPHOCIN PROCESS STABILIZERS

[75] Inventors: Ramanathan Ravichandran, Yonkers; John D. Spivack, Spring Valley, both of N.Y.

[73] Assignee: Ciba-Geigy Corporation, Ardsley, N.Y.

[21] Appl. No.: 180,662

[22] Filed: Mar. 30, 1988

Related U.S. Application Data

[63] Continuation of Ser. No. 98,757, Sep. 17, 1987, abandoned, which is a continuation of Ser. No. 9,116, Jan. 29, 1987, abandoned, which is a continuation of Ser. No. 728,363, Apr. 29, 1985, abandoned.

[51] Int. Cl.$^4$ .............................. C08K 5/34; C07F 9/65
[52] U.S. Cl. ........................................ 524/99; 546/25; 252/400.21
[58] Field of Search ............................ 524/99; 546/25; 252/400.21

[56] References Cited

U.S. PATENT DOCUMENTS

| | | | |
|---|---|---|---|
| 4,141,883 | 2/1979 | Soma et al. | 546/25 |
| 4,185,006 | 1/1980 | Rasberger et al. | 524/99 |
| 4,196,117 | 4/1980 | Spivack | 524/119 |
| 4,259,492 | 3/1981 | Rasberger | 546/21 |
| 4,318,845 | 3/1982 | Spivack et al. | 524/91 |
| 4,374,219 | 2/1983 | Spivack et al. | 524/91 |

FOREIGN PATENT DOCUMENTS 149259  7/1985  European Pat. Off. .............. 546/25

OTHER PUBLICATIONS

Chem. Abst., 79, 127076r, (1973).
Chem. Abst., 82, 73922e, (1975).
Chem. Abst., 82, 87208p, (1975).
Chem. Abst., 68, 12597s, (1968).
Chem. Abst., 73, 15657a, (1970).
Chem. Abst., 75, 13024q, (1971).
P. A. Odovisio et al., Phosphorous & Sulfur, 19, 1, (1984).
G. Sosnovsky et al., Phosphorus, 2, 241, (1973).
M. Konieczny et al., Z. Naturforsch, 33b, 1040, (1977).
G. Sosnovsky et al., Synthesis, 1978, 583.
M. B. Neiman et al., Izu. Akad, Nauk, SSSR, Eng. Ed., 1965, 529.
G. V. Roschenthaler et al., Phosphorus Sulfur, 4, 373, (1978).

*Primary Examiner*—Kriellion Morgan
*Attorney, Agent, or Firm*—Luther A. R. Hall

[57] ABSTRACT

Dibenzodioxaphosphepin and dibenzodioxaphosphocin derivatives are prepared by reacting selected 2,2'-biphenols with phosphorus trichloride in an organic solvent and then reacting the intermediate formed with a 1,4-dihydroxy-2,2,6,6-tetraalkylpiperidine. The phosphites formed are useful as stabilizers of organic polymers and lubricating oils, especially as process stabilizers for polyolefins, elastomers, polyesters and polycarbonates.

18 Claims, No Drawings

6-(1-HYDRO-2,2,6,6-TETRAALKYL-PIPERIDINE-4-OXY)DIBENZODIOXAPHOSPHEPIN AND DIOXAPHOSPHOCIN PROCESS STABILIZERS

This application is a continuation of application Ser. No. 98,757, filed Sept. 17, 1987, now abandoned, which is a continuation of application Ser. No. 9,116, filed Jan. 29, 1987, now abandoned, which is a continuation of application Ser. No. 728,363, filed Apr. 29, 1985 now abandoned.

BACKGROUND OF THE INVENTION

Organic polymeric materials such as plastics and resins and lubricating and mineral oil are subject to thermal, oxidative and photodegradation. A great variety of stabilizers are known in the art for stabilizing various substrates. Their effectiveness varies depending on the causes of degradation and the substrate stabilized. During the course of this work, it was discovered that stabilizers that are very effective long term antioxidants are relatively poor process stabilizers which require stabilization of the substrate against thermal degradation for a short time, but at a relatively high temperature. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

The phosphites of this invention possess an unusual combination of desirable properties as compared to the prior art phosphites which makes these compounds particularly effective and useful as stabilizers.

Phosphites are disclosed in a number of publications. U.S. Pat. No. 4,196,117 discloses biphenyl-cyclic phosphites wherein the phosphorus atom is substituted by O- or S-hydrocarbyl or a hydrocarbyl biphenyl cyclic phosphite group. Soviet Union patent nos. 378,389, 429,070 and 440,390 disclose the stabilization of various polymers with organic phosphites or mixtures including said phosphites wherein the phosphites are methylenebisphenyl cyclic phosphites. Additional 1,1'-biphenyl-2,2'-diyl phosphites are disclosed in Chemical Abstracts, 68, 12597s (1968); 73, 15657a (1970) and 75, 130242q (1971). These various compounds are indicated to be stabilizers of various polymers.

U.S. Pat. Nos. 4,318,845 and 4,374,219 pertain to alkanolamine phosphite esters which are effective as process stabilizers and as color stabilizers and which are resistant to hydrolysis. These phosphite esters do not contain a hindered amine moiety having a free hydroxyl group attached to the 1-N atom of the piperidine group.

The reaction of phosphorochlorodites with alkanolamines is described by P. A. Odorisio et al, Phosphorus and Sulfur, 19, 1 (1984).

U.S. Pat. No. 4,259,492 describes dioxaphosphepines having the phosphorus atom directly substituted by an amine nitrogen. Thus, these materials have a P—N bond and are not tertiary phosphites, but have two ester groups and a phosphorus amide group in the same molecule. This patent generically discloses such dioxaphosphepines having the P—N bond which also contain a hindered amine moiety elsewhere in the molecule, but not compounds having the 1-N atom of the piperidine moiety substituted by hydroxyl.

The instant compounds having a 1-hydroxy hindered amine moiety attached to the P atom of the phosphepin or phosphocin through an oxygen ester linkage are significantly more effective as process stabilizers and color improvers than the compounds of the prior art. The instant compounds additionally provide enhanced light stabilization to the polymer compositions containing said compounds.

The synthesis of various phosphites, phosphinites and phosphinamide structures each containing the 1-oxyl-2,2,6,6-tetramethylpiperidin-4-yl moiety have been reported. [M. Konieczny et al, Phosphorus 2, 241 (1973); ibid, Z. Naturforsch (b) 33, 1040 (1977); ibid, Synthesis 583 (1978); M. B. Neiman et al, Izv. Akad Nauk SSSR, Eng Ed 1965, 529; G. V. Roschenthaler et al, Phosphorus/Sulfur, 4, 373 (1978)]

None of these structures contained the cyclic dibenzodioxaphosphepin or dioxaphosphocin ring system. The reported structures were used as intermediates in the synthesis of selenium compounds or for theoretical academic purposes.

OBJECT OF THE INVENTION

It is the primary object of this invention to provide biphenyl cyclic phosphite compounds which exhibit improved process stabilization performance as contrasted with previously known phosphite compounds.

Various other objects and advantages of this invention will become evident from the following description thereof.

DETAILED DESCRIPTION OF THE INVENTION

The instant invention pertains to a substituted phosphepin or phosphocin compound of formula I

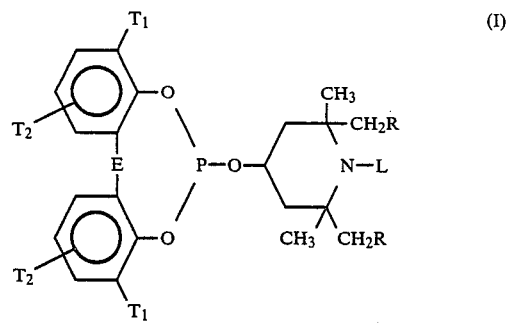

(I)

wherein
$T_1$ and $T_2$ are independently hydrogen, alkyl of 1 to 20 carbon atoms, cycloalkyl of 5 to 6 carbon atoms, aralkyl of 7 to 9 carbon atoms, phenyl or phenyl substituted by 1 to 3 alkyl groups each having 1 to 8 carbon atoms,
E is a direct bond, methylene, alkylidene of 2 to 12 carbon atoms or thio,
L is oxyl or hydroxyl, and
R is hydrogen or methyl.

Preferably the group $T_2$ is in the meta position relevant to $T_1$.

Compounds of especial interest are those wherein $T_1$ and $T_2$ are tert-alkyl of 4 to 8 carbon atoms, and most particularly where $T_1$ and $T_2$ are each tert-butyl.

The compounds where E is a direct bond, methylene or alkylidene of 2 to 4 carbon atoms are preferred.

Most preferably E is a direct bond, methylene or ethylidene.

The compounds where R is hydrogen are also preferred.

The groups $T_1$ and $T_2$ can be independently straight-chain or branched-chain alkyl of 1 to 20 carbon atoms such as for example methyl, ethyl, isopropyl, n-butyl, tert-butyl, tert-amyl, n-hexyl, 2-ethylhexyl, n-octyl, decyl, dodecyl, octadecyl or eicosyl.

When $T_1$ and $T_2$ is cycloalkyl of 5 to 6 carbon atoms, $T_1$ or $T_2$ is for example cyclopentyl or cyclohexyl.

$T_1$ and $T_2$ can also be independently phenyl or alkyl substituted phenyl, such as tolyl, xylyl, mesitylyl, ethylphenyl, 4-butylphenyl, 3,5-dibutylphenyl, p-octylphenyl, 3,5-dioctylphenyl and the like, especially a phenyl group having at least one branched alkyl group, most preferably 2-tert-butylphenyl, 2,4-di-tert-butyl-phenyl, 2,4,6-tri-tert-butylphenyl, 2-tert-butyl-5-methylphenyl, 2,6-di-tert-butyl-phenyl and 2,6-di-tert-butyl-4-methylphenyl, or 2,4-di-tert-octylphenyl.

$T_1$ and $T_2$ can also be independently aralkyl of 7 to 9 carbons such as benzyl, alpha-methylbenzyl or alpha,alpha-dimethylbenzyl.

When $T_1$ and $T_2$ are tert-alkyl of 4 to 8 carbon atoms, $T_1$ and $T_2$ are for example tert-butyl, tert-amyl or tert-octyl, most preferably tert-butyl.

When E is alkylidene of 2 to 12 carbon atoms, E is for example ethylidene, 1,1-propylidene, 1,1-butylidene, 1,1-amylidene, 1,1-octylidene, 1,1-decylidene or 1,1-dodecylidene. Preferably when E is alkylidene, E is ethylidene, 1,1-propylidene or 1,1-butylidene; and most preferably ethylidene.

The alkylated 1,1'-biphenyl-2,2'diyl phosphites and 2,2'-alkylidene-bis(alkylphenyl)phosphites of this invention can be prepared by reacting an alkylated 2,2'-biphenol or an alkylated 2,2'-alkylidene-bis-phenol with phosphorus trichloride optionally in a solvent to give the corresponding phosphorochlorodite which in turn is reacted with 1,4-dihydroxy-2,2,6,6-tetraalkylpiperidine to yield the desired product. The solvent is preferably an aromatic hydrocarbon, such as benzene, toluene, xylene and the like in the presence of a proton acceptor such as a tertiary amine, for example, triethylamine or pyridine. The reaction temperature ranges from room temperature to the reflux temperature of the reaction medium.

The starting materials needed to prepare these phosphites are items of commerce or can be prepared by known methods.

4-Hydroxy-2,2,6,6-tetraalkylpiperidines are described in U.S. Pat. No. 4,014,887. These can be converted to the corresponding 1,4-dihydroxy compounds by oxidation.

The compounds of formula I are effective stabilizers in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from $\alpha,\beta$-unsaturated acids and derivatives thereof, such as polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenyleneisophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyl resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

The compounds of this invention are particularly useful as stabilizers, especially for the protection of polyolefins, for instance, polyethylene, polypropylene, polyisobutylene, poly(butene-1), poly(pentene-1), polyl(3-methylbutene-1), poly(4-methyl-pentene-1), various ethylene-propylene copolymers and the like.

The instant compounds of formula I are particularly effective in stabilizing material subject to oxidative, thermal or light-induced degradation where said material is selected from the group consisting of acrylonitrile-butadiene-styrene (ABS) resins, impact polystyrene, poly(phenylene oxide), polybutadiene, polyisoprene, SBR, natural rubber and lubricating oils.

Other substrates in which the compounds of this invention are particularly useful are polyesters including polyethylene terephthalate and polybutylene terephthalate, including copolymers.

Polyurethanes, polycarbonates, polyamides such as nylon 6, 6/6 and the like as well as copolyamides and polysulfones are also stabilized.

The instant stabilizers are added to the plastics or oil in a concentration of 0.01 to 5% by weight, calculated relative to the material to be stabilized. Preferably, 0.1 to 2.5% by weight of the stabilizer calculated relative to the material to be stabilized, is incorporated into the latter.

Incorporation can be effected after polymerization, for example by mixing the compounds and, if desired, further additives into the melt by the methods customary in the art, before or during shaping, or by applying the dissolved or dispersed compounds to the polymer, with subsequent evaporation of the solvent if necessary.

The stabilizers can also be added to the plastics to be stabilized in the form of a master batch which contains these compounds, for example in a concentration of 2.5 to 25% by weight.

Although the compounds of the invention may be used to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.01 to about 5% by weight of the stabilized composition, although this will vary with the particular substrate and application. An advantageous range is from about 0.1 to about 2.5%.

The stabilizers of formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.05 to about 5%, preferably from about 0.1 to about 2.5% by weight of various conventional additives, such as the following, particularly phenolic antioxidants or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)malonate, di-dodecylmercapto-ethyl 2,2-bis-(3,5-di-tert.-butyl-4-hydroxybenzyl)-malonate and di-[4-(1,1,3,3-tetramethylbutyl)-phenyl]2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethyl-benzene, 1,4-di-(3,5-di-tert-butyl-4-hydroxybenzyl)-2,3,5,6-tetramethylbenzene and 2,4,6-tri-(3,5-di-tert.-butyl-4-hydroxy-benzyl)-phenol.

1.8 s-Triazine compounds, such as, for example 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxphenylethyl)- s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acids, such as, for example 1,3,5-tris-(3,5,-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine, N,N'-bis-β-(3,5-di-t-butyl-4-hydroxyphenyl)propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol;. 1,9-nonanediol, ethylene glycol, 1,2-propane-diol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenyl)propionic acid with monohydric or polyhydric alcohols, such as for example, with methanol, ethanol, octadecanol, 1,6-hexanediol, 1-9-nonanediol, ethylene glycol, 1,2-propanediol, di-ethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2.]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane, especially the tetrakis ester of pentaerythritol.

1.13 Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-pentamethylpiperidyl) sebacate, bis-(1,2,2,6,6-pentamethylpiperidyl) 2-n-butyl-2-(2-hydroxy-3,5-di-tert-butylbenzyl)malonate or 3-n-octyl-7,7,9,9-tetra-methyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.butyl-oxanilide, 2,2'-didodecycloxy-5,5'-di-tert.-butyl-oxanilide, 2-ethoxy-2'-ethyloxanilide, N,N'-bis-(3-dimethyl-aminopropyl)-oxalamide, 2-ethoxy-5-tert.-butyl-2'-ethyl-oxanilide and the mixtures thereof with 2-ethoxy-2'-ethyl-5,4'-di-tert.-butyl-oxanilide, or mixture of ortho- and para-methoxy- as well as of o- and p-ethoxy-di-substituted oxanilides.

3. Metal deactivators, e.g., oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilizers, e.g. alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl)diphenylene-4,4'-bis-(phosphonite).

Other additives that can be incorporated in the stabilized compositions are thiosynergists, such as dilauryl thiodiproprionate, lubricants such as stearyl alcohol, fillers, asbestos, kaolin, talc, glass fibers, pigments, optical brighteners, flameproofing agents and antistatic agents.

Compositions where the organic material is a synthetic polymer and particularly a polyolefin homopolymer or copolymer are of especial interest.

Such compositions may additionally contain from about 0.01 to about 5% by weight, of the total composition, of a phenolic antioxidant.

The phenolic antioxidants of particular interest is one selected from the group consisting of 2,6-di-tert-butyl-4-methylphenol, 4,4'-thio-bis(6-tert-butyl-3-methylphenol), 2,2'-methylene-bis(6-tert-butyl-4-methylphenol), 4,4'-methylene-bis-(2,6-di-tert-butyl-phenol), 1,1,3-tris-(5-tert-butyl-4-hydroxy-2-methylphenyl)-butane, 1,3,5-tris-(3,5-di-tert-butyl-4-hydroxybenzyl)2,4,6-trimethylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentanetetrayl tetrakis(3,5-di-tert-butyl-4-hydroxyhydrocinnamate), 1,3,5-tris(3,5-di-tert-butyl-4-hydroxybenzyl)isocyanurate and thiodiethylene bis(3,5-di-tert-butyl-4-hydroxyhydrocinnamate).

Another object of the instant invention is a method of stabilizing an organic material against oxidative, thermal and actinic degradation which comprises incorporation into said organic material an effective stabilizing amount of a compound of formula I.

The following examples are presented for the purpose of illustration only and are not to be construed to limit the nature or scope of the instant invention in any manner whatsoever.

EXAMPLE 1

2,4,8,10-Tetra-tert-butyl-6-[1-hydroxy-2,2,6,6-tetramethylpipieridin-4-yloxy]-dibenzo[d,f][1,3,2]dioxaphosphepin In a flame-dried flask under nitrogen, 4.4 ml of phosphorous trichloride in 100 ml of dry toluene is treated with a solution of 20.54 grams of 3,3,',5,5'-tetra-tert-butyl-biphenyl-2,2'-diol and 13.9 ml of triethylamine in 80 ml of toluene at a temperature not exceeding 5° C.

The reaction is stirred at ambient temperature for 12 hours and the precipitated salt is removed by filtration. The filtrate is evaporated under reduced pressure and the residue is dissolved in 200 ml of dry tetrahydrofuran and treated with 17.01 grams of 1,4-dihydroxy-2,2,6,6-tetramethylpiperidine and 14.0 ml of triethylamine in 100 ml of dry tetrahydrofuran. After stirring the mixture at room temperature for 12 hours, the mixture is filtered and the filtrate concentrated under reduced pressure. The residue is crystallized from acetonitrile to give 31.3 grams of a pale pink powder, m.p. 183°–185° C.

Analysis: Calculated for: $C_{37}H_{58}NO_4P$: C, 72.63; H, 9.56; N, 2.29. Found: C, 72.9; H, 9.3; N, 2.0.

EXAMPLE 2

2,4,8,10-Tetra-tert-butyl-6-[1-hydroxy-2,2,6,6-tetramethylpiperidin-4-yloxy]-dibenzo[d,g][1,3,2]dioxaphosphocin The above-named compound is prepared by the general procedure of Example 1 by reacting 8.8 ml of phosphorous trichloride, 42.54 grams of 2,2'-methylene bis-(4,6-di-tert-butylphenol), 36.8 ml of triethylamine and 11.03 grams of 1,4-dihydroxy-2,2,6,6-tetramethylpiperidine.

The reaction product is recrystallized from acetonitrile to give 26.0 grams of a white powder, m.p. 145°–147° C.

Analysis: Calculated for: $C_{38}H_{60}NO_4P$: C, 72.92; H, 9.66. Found: C, 72.9; H, 9.7.

EXAMPLE 3

2,4,8,10-Tetra-tert-butyl-6-[1-hydroxy-2,2,6,6-tetramethylpiperidin-4-yloxy]-12-methyl-12H-dibenzo[d,g][1,3,2]-dioxaphosphocin The above-named compound is prepared using the general procedure of Example 1 by reacting 4.4 ml of phosphorous trichloride, 21.94 grams of 2,2'-ethylidenebis(4,6-di-tert-butylphenol), 19.3 ml of triethylamine and 6.68 grams of 1,4-dihydroxy-2,2,6,6-tetramethylpiperidine.

The produce is recrystallized from toluene to give a white powder (13.1 grams), m.p. 250°–252° C.

Analysis: Calculated for: $C_{39}H_{62}NO_4P$: C, 73.20; H, 9.71; N, 2.19. Found: C, 73.0; H, 9.9; N, 2.3.

EXAMPLE 4

2,4,8,10-Tetra-tert-butyl-6-[1-oxyl-2,2,6,6-tetramethylpiperidin-4-yloxy]-dibenzo[d,g][1,3,2]dioxaphosphocin In a flame-dried flask under nitrogen, 4.4 ml of phosphorous trichloride in 100 ml of dry toluene is treated with a solution of 21.27 grams of 2,2'-methylene-bis-(4,6-di-tert-butylphenol) and 13.9 ml of triethylamine in 80 ml of toluene at a temperature not exceeding 5° C. The reaction is stirred at ambient temperature for 12 hours and the suspension is cooled to 5° C. The mixture is treated with 8.61 grams of 4-hydroxy-1-oxyl-2,2,6,6-tetramethylpiperidine and 7 ml of triethylamine in 100 ml of dry toluene. After stirring the mixture at room temperature for 12 hours, the mixture is filtered and the filtrate concentrated under reduced pressure. The residue is crystallized from acetonitrile to give 17.0 grams of a pale red solid.

Analysis: Calculated for: $C_{38}H_{59}NO_4P$: C, 73.04; H, 9.52. Found: C, 73.8; H, 9.9.

EXAMPLE 5

2,4,8,10-Tetra-tert-butyl-6-[1-oxyl-2,2,6,6-tetramethylpiperidin-4-yloxy]-dibenzo[d,f][1,3,2]dioxaphosphepin The above-named compound is prepared by the general procedure of Example 1 by reacting 4.4 ml of phosphorous trichloride, 20.54 grams of 20.9 ml of triethylamine and 8.61 grams 4-hydroxy-1-oxyl-2,2,6,6-tetramethylpiperidine.

The reaction product is recrystallized from heptane to give the title compound, m.p. 172°–175° C.

Analysis: Calculated for: $C_{37}H_{57}NO_4P$: C, 72.75; H, 9.5; N, 2.3. Found: C, 72.4; H, 9.5; N, 2.2.

EXAMPLE 6

Processing Stability of Polypropylene at 500° F. (260° C.)

Base Formulation:
Profax 6501 (Himont): 100 parts
Calcium stearate: 0.10 parts

Stabilizers are solvent blended into polypropylene as solutions in methylene chloride and, after removal of the solvent by evaporation at reduced pressure, the resin is extruded using the following extruder conditions:

|  | Temperature | |
| --- | --- | --- |
|  | (°F.) | (°C.) |
| Cylinder #1 | 450 | 232 |
| Cylinder #2 | 475 | 246 |
| Cylinder #3 | 500 | 260 |
| Gate #1 | 500 | 260 |
| Gate #2 | 500 | 260 |
| Gate #3 | 500 | 260 |
| RPM | 100 | |

After each of the first, third and fifth extrusions, resin pellets are compression molded into 125 mil (3.2 mm) thick plaques at 380° F. (193° C.) and specimen yellowness index (Y.I.) determined according to ASTM D1925-63T.

The melt flow rate (MFR) is determined by ASTM method 1238 condition L. The melt flow rate is a measure of the molecular weight for a specific type of polymer. The data is presented in Table I:

TABLE I

| Additive (% by weight) | MFR (g/10 min)** After Ext. | | | YI Color*** After Extrusion | | |
| --- | --- | --- | --- | --- | --- | --- |
|  | 1 | 3 | 5 | 1 | 3 | 5 |
| None | 7.3 | — | 12.7 | 0.8 | 0.3 | 0.2 |
| 0.1 Antiox. A* | 3.9 | — | 5.1 | 3.2 | 5.2 | 6.7 |
| The following contain 0.1% Antioxidant A and a compound as indicated below: | | | | | | |
| 0.05 Cmpd. Ex. 1 | 2.5 | 0 | 2.7 | 0.8 | 1.0 | 2.0 |
| 0.05 Cmpd. Ex. 2 | 2.3 | 0 | 2.8 | 1.9 | 3.3 | 2.9 |

*Antioxidant A is neopentanetetrayl tetrakis-(3,5-di-tert-butyl-4-hydroxyhydrocinnamate)
**Melt Flow Rate
***Yellowness Index

EXAMPLE 7

Light Stabilization of Poly(phenylene oxide)

The base resin is poly(phenylene oxide) obtained as Noryl N190 (General Electric).

Stabilizers are solvent blended into poly(phenylene oxide) as solutions in methylene chloride and, after removal of the solvent by evaporation at reduced pressure for 2 hours at 110° C., the resin is extruded using the following extruder conditions:

|  | Temperature | |
| --- | --- | --- |
|  | (°F.) | (°C.) |
| Cylinder #1 | 450 | 232 |
| Cylinder #2 | 455 | 235 |
| Cylinder #3 | 455 | 235 |
| Gate #1 | 460 | 238 |
| Gate #2 | 460 | 238 |
| Gate #3 | 460 | 238 |
| RPM | 200 | |

The extruded resin is then compression molded into 125 mil (3.2 mm) thick plaques for color evaluation after exposure in a Xenon Arc Fadeometer at a temperature of 63±3° C. at a relative humidity of 25–35% with samples being exposed under ⅛" (3.2 mm) glass. The specimen yellowness index (YI) is determined according to ASTM D1925-63T. The data are given in the table below.

| Stabilizer (% by weight) | Change in Yellowness Index Upon Hours Exposure in Xenon Arc Fadeometer | | | | |
| --- | --- | --- | --- | --- | --- |
|  | 60 | 129 | 205 | 307 | 405 |
| Base resin | 1.3 | 1.9 | 5.4 | 15.0 | 23.3 |
| Base resin plus 1% UV absorber$^a$ plus 0.5% of Compound of |  |  |  |  |  |
| Example 2 | 3.2 | 3.2 | 2.1 | 4.9 | 10.3 |
| Example 3 | 3.5 | 3.3 | 2.5 | 4.7 | 9.3 |

$^a$UV-absorber is 2-(2-hydroxy-3,5-di-tert-amylphenyl)-2H—benzotriazole

These data show that the poly(phenylene oxide) compositions containing an instant hydroxylamine stabilizer exhibit markedly reduced discoloration upon exposure to light.

EXAMPLE 8

When a substrate selected from the group consisting of ABS resins, IPS (impact polystyrene), polybutadiene, polyethylene, SBR, polyisoprene, natural rubber, poly(phenylene oxide), polypropylene, hydrocarbon lubricating oils and synthetic oils contains an effective amount of a compound of instant Example 1, 2, 3, 4 or 5, the substrate is stabilized against degradation compared to the unstabilized substrate.

What is claimed is:

1. A compound of formula I

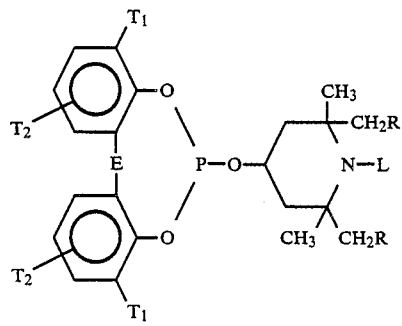

wherein
$T_1$ and $T_2$ are independently hydrogen, alkyl of 1 to 20 carbon atoms, cycloalkyl of 5 to 6 carbon atoms, aralkyl of 7 to 9 carbon atoms, phenyl or phenyl substituted by 1 to 3 alkyl groups each having 1 to 8 carbon atoms,
E is a direct bond, methylene, alkylidene of 2 to 12 carbon atoms or thio,
L is hydroxyl, and
R is hydrogen or methyl.

2. A compound according to claim 1 wherein $T_2$ is in the meta position relevant to $T_1$.

3. A compound according to claim 2 wherein $T_1$ and $T_2$ are tert-alkyl of 4 to 8 carbon atoms.

4. A compound according to claim 3 wherein $T_1$ and $T_2$ are each tert-butyl.

5. A compound according to claim 1 wherein E is a direct bond, methylene or alkylidene of 2 to 4 carbon atoms.

6. A compound according to claim 5 wherein E is a direct bond, methylene or ethylidene.

7. A compound according to claim 1 wherein R is hydrogen.

8. The compound according to claim 1 which is 2,4,8,10-tetra-tert-butyl-6-[1-hydroxy-2,2,6,6-tetramethylpiperidin-4-yloxyl]-dibenzo[d,f][1,3,2]dioxaphosphepin.

9. The compound according to claim 1 which is 2,4,8,10-tetra-tert-butyl-6-[1-hydroxy-2,2,6,6-tetramethylpiperidin-4-yloxy]-dibenzo[d,g][1,3,2]dioxaphosphocin.

10. The compound according to claim 1 which is 2,4,8,10-tetra-tert-butyl-6-[1-hydroxy-2,2,6,6-tetramethylpiperidin-4-yloxy]-12-methyl-12H-dibenzo[d,g][1,3,2]dioxaphosphocin.

11. A composition of matter comprising an organic material subject to oxidative, thermal and actinic degradation stabilized with from about 0.01 to about 5% by weight, of the total composition, of a compound of claim 1.

12. A composition of claim 11 wherein the organic material is a synthetic polymer.

13. A composition of claim 12 wherein the polymer is a polyolefin homopolymer or copolymer.

14. A composition of claim 11 which additionally contains from about 0.01 to about 5% by weight, of the total composition, of a phenolic antioxidant.

15. A composition of claim 14 wherein the phenolic antioxidant is selected from the group consisting of 2,6-di-tert-butyl-4-methylphenol, 4,4'-thio-bis(6-tert-butyl-3-methylphenol), 2,2'-methylene-bis(6-tert-butyl-4-methylphenol), 4,4[-methylene-bis-(2,6-di-tert-butylphenol), 1,1,3-tris(5-tert-butyl-4-hydroxy-2-methylphenyl)-butane, 1,3,5-tris(3,5-di-tert-butyl-4-hydroxybenzyl)-2,4,-6-tri-methylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentanetetrayl tetrakis-(3,5-di-tert-butyl-4-hydroxyhydrocinnamate), 1,3,5-tris(3,5-di-tert-butyl-4-hydroxybenzyl)isocyanurate and thiodiethylene bis(3,5-di-tert-butyl-4-hydroxyhydrocinnamate).

16. A composition according to claim 11 wherein the organic material is selected from the group consisting of acrylonitrile-butadiene-styrene (ABS) resins, impact polystyrene, polyethylene, polypropylene, poly(phenylene oxide), polybutadiene, polyisoprene, SBR, natural rubber and lubricating oils.

17. A composition according to claim 16 wherein the organic material is poly(phenylene oxide).

18. A method for stabilizing an organic material against oxidative, thermal and actinic degradation which comprises incorporating into said organic material an effective stabilizing amount of a compound of claim 1.

* * * * *